United States Patent [19]

Howard

[11] Patent Number: 4,832,830
[45] Date of Patent: May 23, 1989

[54] METHOD FOR OLEFINIC SEPARATION

[75] Inventor: Lee J. Howard, Emmaus, Pa.

[73] Assignee: Air Products and Chemicals, Inc., Allentown, Pa.

[21] Appl. No.: 104,321

[22] Filed: Oct. 2, 1987

[51] Int. Cl.[4] .............................................. F25J 3/02
[52] U.S. Cl. ...................................... 208/351; 62/11; 62/29; 208/354; 208/355
[58] Field of Search .............. 208/351, 353, 354, 356, 208/355; 62/11, 24, 29, 32; 585/500, 601

[56] References Cited

U.S. PATENT DOCUMENTS 4,430,102  2/1984  Tedder ...................................... 62/24
4,600,421  7/1986  Kummann ........................... 62/29 R
4,664,607  5/1987  Bauer ........................................ 62/29

Primary Examiner—Glenn Caldarola
Attorney, Agent, or Firm—Willard Jones, II; James C. Simmons; William F. Marsh

[57] ABSTRACT

A process and apparatus for separating selected $C_4$ olefinic products from combinations thereof with lower boiling point compounds comprises partially condensing a stream containing said products and compounds, atmospherically separating said partially condensed stream to yield gas and liquid streams, stipping said liquid stream to yield stripper overhead gas and stripper bottoms liquids, and recovering said $C_4$ olefinic and paraffinic products from said stripper bottoms liquid, all at selected temperatures and pressures adapted to produce a high recovered percentage of said desired $C_4$ olefinic and paraffinic product.

2 Claims, 1 Drawing Sheet

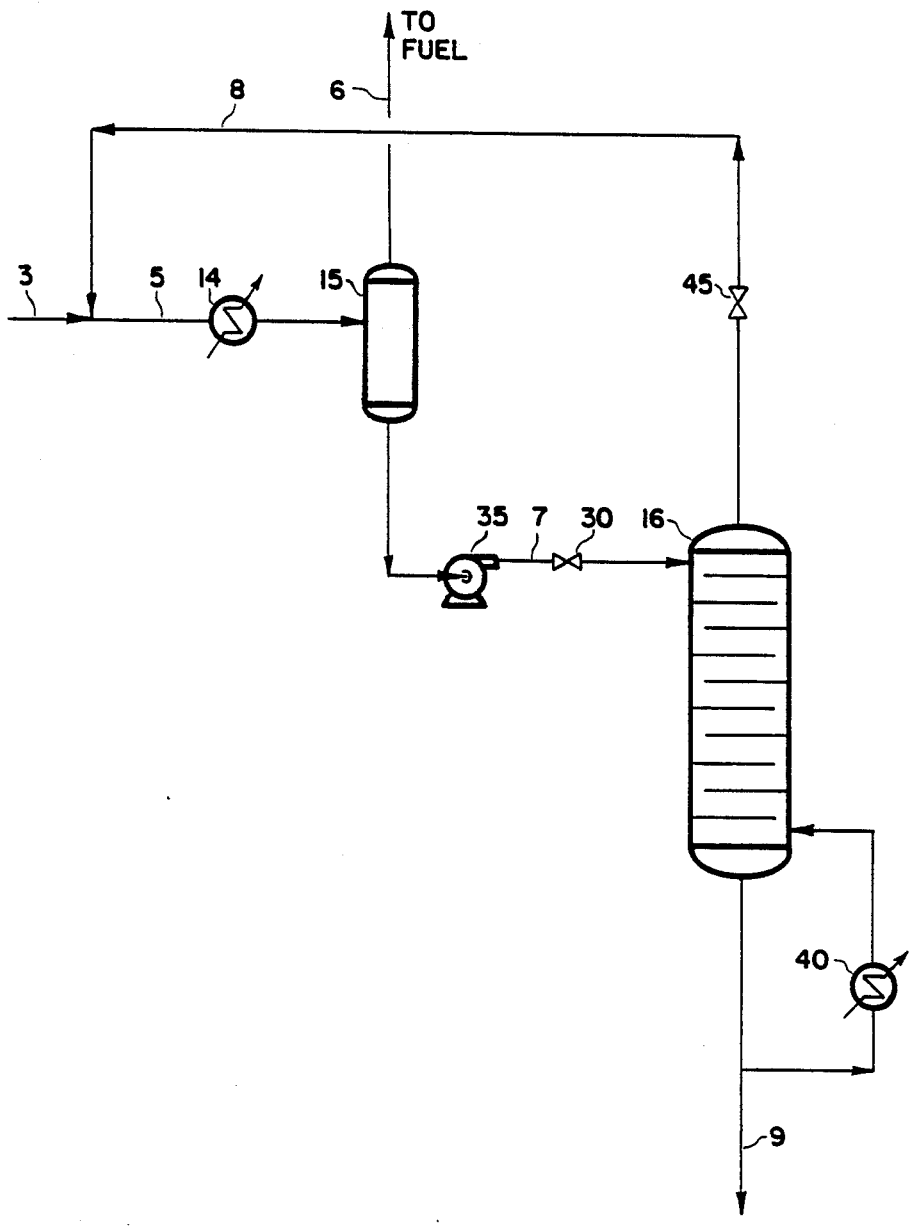

METHOD FOR OLEFINIC SEPARATION

TECHNICAL FIELD

The present invention pertains to the separation of $C_4$ olefinic and paraffinic products from lower boiling point compounds in an effective and efficient manner.

BACKGROUND OF THE INVENTION

Olefinic products, referred to generally herein as $C_4$ olefins or as olefinic products, are commonly produced in catalytic dehydrogenation processes using propane, butane, pentane, or mixed paraffins as starting materials. Such processes include the CATOFIN TM and CATADIENE TM processes developed commercially by Air Products and Chemicals, Inc. of Allentown, Pa, the assignee of the present application. Product streams from these dehydrogenation processes usually also include lighter or higher boiling point gases than the desired olefinic product.

Typically, the olefinic product has been separated from the lighter gases in such streams, in the past, by a product separation sequence which included pressurization of the olefinic-rich stream, absorption of the lighter gases from that stream (in an absorption medium such as heavy oil) and then the stripping of the lighter gases from the absorption medium by distillation. Because absorption took place in this process in the vapor phase, entrained liquid was typically removed during and after compression by simply permitting such entrained liquid to collect and condense as the vapors passes through a drum or small tank, sometimes referred to as a "flash drum" or "knockout drum." This combination of absorber/stripper and distillation column for stabilizing (or "deethanizing" or "depropanizing" as it is sometimes referred to) the product stream is effective to recover a high proportion of the available olefinic product in the feed stream. Cryogenic recovery has also been used, to accomplish the same result, in place of absorption/stripping.

However, the cost effectiveness of these stabilizing processes is greatly impaired by the required size and energy demands of the absorber/stripper (or cyrogenic system) and the volume of material recycled to the process.

It has now been found that the depropanizer vapor overhead stream, which has heretofore been recycled into the compression section of the process, may be more economically separated and recovered by a process of condensation and fractionation. Such a process eliminates the need to recycle vapor for compression in the product compression stage, thus permitting both energy and capital cost savings.

BRIEF DESCRIPTION OF THE INVENTION

In the process and apparatus of the present invention, $C_4$ olefinic and paraffinic product is separated from lighter olefinic and paraffinic compounds by partial condensation, followed by flash separation techniques to produce gas and liquid streams. The liquid stream is subsequently stripped to remove light ends and $C_4$ olefinic and paraffinic products are recovered in the stripper bottoms.

Partial condensation of the product stream is carried out at approximately 30° F. and 90 psi. Stripping of the liquid stream is carried out in a stripper having from 20 to 30 trays and operated at a temperature range of 55° to 110° F. and a pressure range of 95 to 115 psi.

For a better understanding of this invention, reference is made to the detailed description which follows, together with the accompanying figure and subjoined claims.

BRIEF DESCRIPTION OF THE FIGURES

The FIGURE is a schematic diagram of the process and apparatus of the present invention as used or adapted for the separation of $C_4$ olefinic products from lighter gases mixed therewith.

DETAILED DESCRIPTION OF THE INVENTION

As illustrated in the figure, in the process and apparatus of the present invention, the feed stream is a gas mixture typically including desired $C_4$ olefinic and paraffinic product along with lower boiling point compounds such as $C_3$, $C_2$, and $C_1$ hydrocarbons, carbon oxides, hydrogen, and other trace components. Such a stream may be produced, for example, in an upstream dehydrogenation process such as Air Products' CATOFIN TM or CATADIENE TM processes; the feed comprises the cooled reactor output from such processes. In the present process, that mixed gas feed stream 3 is treated for separation of the $C_4$ olefinic and paraffinic product by the following process.

In contrast to the prior art designs of the depropanizer tower in the above processes, which require two-stage condensing systems or reabsorbers in addition to extensive stream recycles in order to limit the loss of $C_4$ olefinic and paraffinic products, the present invention allows recovery of said $C_4$ olefinic and paraffinic products by a method which requires no recycling of streams from the overhead system back into the process.

After partial condensation of the depropanizer overhead vapors, the remaining vapor is directed via line 3 to secondary refrigerated condenser 14. Prior to entering condenser 14, recycled vapors are admixed with the stream 3 to yield stream 5. The partially condensed stream exiting condenser 14 is directed to a separation vessel 15 to produce a lean gas and a liquid. The lean gas overhead is directed via line 6 to be used as fuel while the liquid is directed to pump 35 and then via line 7 to stripper 16. Line 7 is controlled by level control valve 30. The liquid conveyed by line 7 is composed of light ends and $C_4$ olefinic and paraffinic products and is pumped onto the top tray of stripper 16 in order to distill the desired $C_4$ components from the stripper vapors.

Stripper 16 is typically comprised of 20 to 30 trays and is operated at a temperature of from 55° l to 110° F. and a pressure of 95 to 115 psi. Stripper vapors are conveyed via line 8 with stripper overhead pressures regulated by valve 45. A portion of stripper liquid is recycled through stripper reboiler 40 which is operated at 110° F. The remainder of stripper liquid stream 9 is rich in desirable $C_4$ olefinic and paraffinic products and is the product stream of the present invention. Stripper vapor stream 8 is recycled and admixed with stream 3 to yield stream 5.

While the intermediate stream pressure and temperature parameters in the process of the present invention may be varied in order to adapt the process and apparatus to most efficient recovery of the desired olefinic product from a given feed stream, a determination and selection of these process parameters may easily be made by those skilled in the art, depending on the specific feed stream at hand, and the desired product. In order to assist in this determination and selection and to illustrate typical process parameters for specific processes, the following is a calculated example of the process of the present invention:

Example 1

A typical process stream from the Air Products $C_4$ CATADIENE TM process is delivered to the apparatus of the present invention via line 3. The process parameters including mole percent composition of certain identified streams, as well as temperature and pressure, are summarized in Table 1 below, where streams and vessels are identified with the reference numerals of the figure.

The $C_4$ portions of the feed stream (3) and product stream (9) contains roughly equal amounts of olefinic and paraffinic products, while the $C_3$ portion of the feed stream is about 85% olefinic and the $C_2$ portion about 40% olefinic. Ultimately the olefinic portion of the $C_4$ product stream is reacted and the remaining paraffinic portion is recycled to the feed of the dehydrogenation process.

TABLE 1

| Stream: | 3 | 8 | 5 | 6 | 7 | 9 |
|---|---|---|---|---|---|---|
| Inerts | 3 | <1 | 2 | 4 | <1 | — |
| $C_2-$ | 10 | 4 | 7 | 16 | 4 | — |
| $C_3$ | 71 | 92 | 83 | 78 | 85 | <1 |
| $C_4$ | 16 | 3 | 8 | 2 | 11 | 99+ |
| Temp (°F.) | 66 | 55 | 56 | 30 | 30 | 110 |
| Pressure (PSIA) | 95 | 115 | 95 | 90 | 90 | 115 |

The above data suggests that the method of the present invention permits a high degree of $C_4$ recovery while minimizing $C_3-$ byproduct production and recycle requirements. This, in turn, has the overall effect of improving process efficiency and reducing capital costs (due to smaller compression requirements).

Statement of Industrial Utility

The present invention is expected to be useful in the cost effective separation of $C_4$ olefinic and paraffinic products from streams thereof including lower boiling point compounds. Such streams are typically produced in commercial paraffin dehydrogenation processes such as the CATOFIN TM and CATADIENE TM processes of Air Products and Chemicals, Inc.

I claim:

1. In a process for the separation and removal of $C_4$ olefinic and paraffinic hydrocarbon species from a gas stream comprising $C_4$ olefinic and paraffinic hydrocarbon species, $C_3$ hydrocarbon species and other light gases, wherein the gas stream is produced as at least a portion of overhead from a depropanizer in a process for the dehydrogenation of paraffins to produce mono- and di- olefins, the improvement for separating the $C_4$ olefinic and paraffinic hydrocarbon species from the gas stream comprises:

(a) cooling the gas stream to below 30° F. at about 90 psi, thereby partially condensing the gas stream;

(b) separating the partially condensed gas stream at about 30° F. and about 90 psi, to produce a liquid stream and a lean gas exhaust stream comprising at least a portion of the $C_3$ hydrocarbon species and other light gases;

(c) stripping the liquid stream produced in step (b) in a stripper at about 55°–110° F. and about 95-115 psi thereby producing an overhead stream comprising substantially $C_3$ olefinic hydrocarbon species and a bottoms stream comprising substantially $C_4$ olefinic and paraffinic hydrocarbon species;

(d) recycling the overhead stream produced in step (c) to step (a); and (e) recovering at least a portion of the bottoms stream produced in step (c) as a substantially $C_4$ olefinic and paraffinic product stream.

2. The process of claim 1, wherein the stripper comprises an atmospheric separation tower having from 20 to 30 trays.

* * * * *

UNITED STATES PATENT AND TRADEMARK OFFICE
CERTIFICATE OF CORRECTION

PATENT NO. : 4,832,830

DATED : May 23, 1989

INVENTOR(S) : Lee J. Howard

It is certified that error appears in the above-identified patent and that said Letters Patent is hereby corrected as shown below:

Column 4, line 12, "C4olefinic" should read -- $C_4$ olefinic --.

Column 4, line 31, "C3olefinic" should read -- $C_3$ olefinic --.

Signed and Sealed this

Thirtieth Day of January, 1990

*Attest:*

JEFFREY M. SAMUELS

*Attesting Officer*     *Acting Commissioner of Patents and Trademarks*